(12) United States Patent
Nakagawa et al.

(10) Patent No.: US 10,453,209 B2
(45) Date of Patent: Oct. 22, 2019

(54) MODELING METHOD AND APPARATUS

(71) Applicants: FUJITSU LIMITED, Kawasaki-shi, Kanagawa (JP); The University of Tokyo, Tokyo (JP)

(72) Inventors: Machiko Nakagawa, Kawasaki (JP); Masaki Kazama, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 501 days.

(21) Appl. No.: 14/918,824

(22) Filed: Oct. 21, 2015

(65) Prior Publication Data
US 2016/0140418 A1   May 19, 2016

(30) Foreign Application Priority Data
Nov. 18, 2014   (JP) .................. 2014-233878

(51) Int. Cl.
   *G06T 7/60*   (2017.01)
   *G16H 50/50*   (2018.01)
(52) U.S. Cl.
   CPC .............. *G06T 7/60* (2013.01); *G16H 50/50* (2018.01)
(58) Field of Classification Search
   None
   See application file for complete search history.

(56) References Cited

U.S. PATENT DOCUMENTS

| | | | | |
|---|---|---|---|---|
| 5,343,391 A | * | 8/1994 | Mushabac | A61C 13/0004 433/72 |
| 5,469,850 A | * | 11/1995 | Iizuka | G06F 19/3437 600/443 |
| 6,587,711 B1 | * | 7/2003 | Alfano | A61B 5/0068 600/410 |

(Continued)

FOREIGN PATENT DOCUMENTS

| | | |
|---|---|---|
| JP | 2013-15945 | 1/2013 |
| JP | 2015-128546 | 7/2015 |

OTHER PUBLICATIONS

Yutaka Ohtake et al. "A Multi-scale Approach to 3D Scattered Data Interpolation with Compactly Supported Basis Functions", Shape Modeling International, 2003, IEEE, 2003, 9 pages.

*Primary Examiner* — Jiangeng Sun
(74) *Attorney, Agent, or Firm* — Xsensus LLP

(57) ABSTRACT

A disclosed modelling method includes: calculating a first function for generating data of a closed surface that contains plural points representing an annular structure in an object, based on positional information of the plural points; generating data of a first point set representing a boundary of the object, from tomographic image data; detecting data of points which are included in the first point set and located inside the closed surface by using the first function; removing the detected data of points from the data of the first point set to generate data of a second point set; calculating a second function for generating data of a shape of the object using the data of the second point set and data of the plural points; and storing data of the shape of the object, which is generated by using the second function, in the memory.

8 Claims, 23 Drawing Sheets

(56) References Cited

U.S. PATENT DOCUMENTS

| | | | |
|---|---|---|---|
| 2005/0219245 A1* | 10/2005 | Tao | G06T 17/20 345/424 |
| 2006/0104969 A1* | 5/2006 | Oray | A61K 33/14 424/94.63 |
| 2013/0002677 A1 | 1/2013 | Hatanaka et al. | |
| 2015/0193930 A1 | 7/2015 | Nakagawa et al. | |

* cited by examiner

US 10,453,209 B2

MODELING METHOD AND APPARATUS

CROSS-REFERENCE TO RELATED APPLICATIONS

This application is based upon and claims the benefit of priority of the prior Japanese Patent Application No. 2014-233878, filed on Nov. 18, 2014, the entire contents of which are incorporated herein by reference.

FIELD

This invention relates to a modeling apparatus, a modeling method, and a modeling program.

BACKGROUND

Organ simulators to simulate dynamics of organs have been developed, and it is expected that such organ simulators are used for diagnosis, determination of a treatment policy, prediction of postoperative condition and the like. It is favorable that an organ shape used for simulation is analogous to an actual organ shape to the extent possible, in order to make the reliability of the simulator higher.

An organ shape differs from patient to patient, and using a uniform shape is not allowed. Therefore, an organ shape used in simulation is generated for each patient. However, because organs exist in a human body and they are invisible and directly unmeasurable, they are generated based on patient's medical images such as CT (Computed Tomography) images or MRI (Magnetic Resonance Imaging) images. A certain document discloses a technique to generate an organ shape of a patient by transforming a template representing a standard shape of an organ based on landmarks deployed on patient's medical images.

However, a technique to generate an organ shape with attention to an annular structure in the organ is unknown. For example, a heart has a pulmonary valve, an aortic valve, a mitral valve and a tricuspid valve. And an edge of each valve is called a valve annulus. Because the valve annulus plays an important role when a heart serves as a pump, generating a high-accuracy shape in the vicinity of the valve annulus makes the reliability of the simulation higher.

Patent Document 1: Japanese Laid-open Patent Publication No. 2013-015945

Non-Patent Document 1: "A Multi-scale Approach to 3D Scattered Data Interpolation with Compactly Supported Basis Functions", Yutaka Ohtake, Alexander Belyaev, and Hans-Peter Seidel, Shape Modeling International 2003, Seoul, Korea, May 2003, pp 153-161

In other words, there is no technique to generate a high-accuracy shape of an object including an annular structure.

SUMMARY

A modelling apparatus relating to this invention includes: a memory; and a processor configured to use the memory and execute a process. And the process includes: first calculating a first function for generating data of a closed surface that contains plural points that represent an annular structure in an object, based on positional information of the plural points; generating data of a first point set that represents a boundary of the object, from data of plural tomographic images in each of which a first area occupied by the object is designated; detecting data of points which are included in the first point set and located inside the closed surface by using the first function; removing the detected data of points from the data of the first point set to generate data of a second point set; second calculating a second function for generating data of a shape of the object using the data of the second point set and data of the plural points; and storing data of the shape of the object, which is generated by using the second function, in the memory.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

DESCRIPTION OF EMBODIMENTS

Embodiment 1

In the first embodiment, an example in which a shape of an object is divided by a surface that passes through landmarks deployed annularly is explained.

Figure 1:
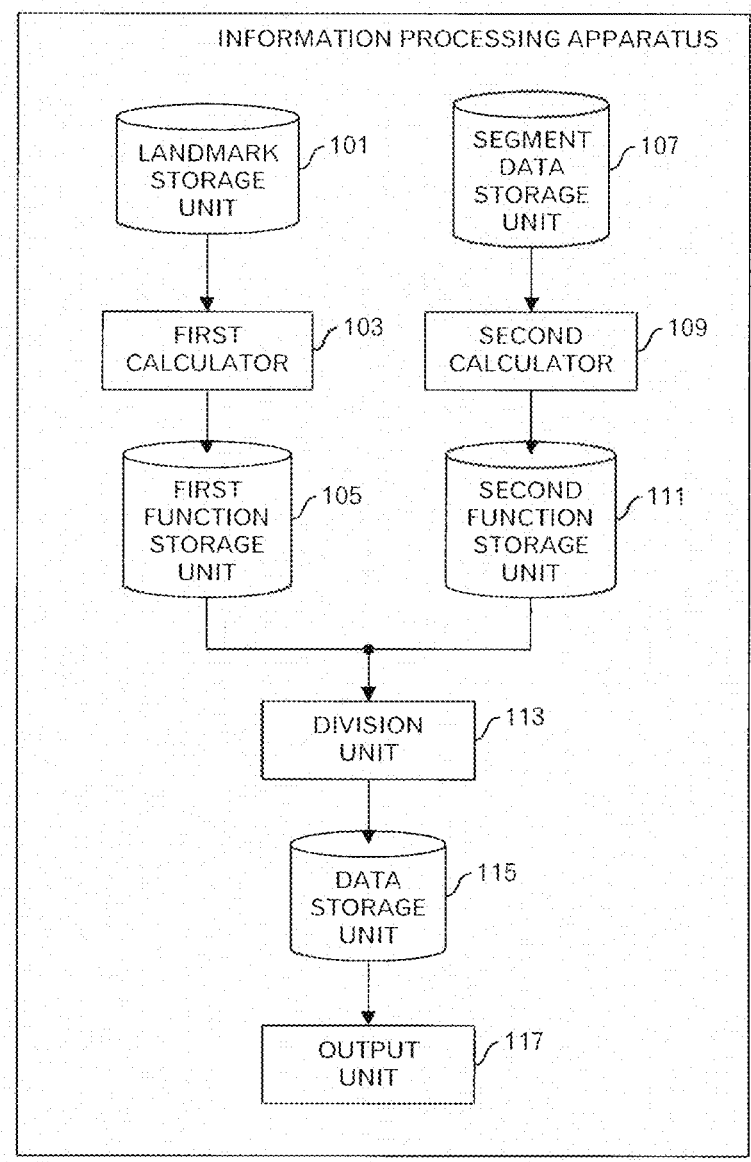
FIG. 1 is a diagram depicting a functional block diagram of an information processing apparatus in a first embodiment.

FIG. 1 illustrates a functional block diagram of an information processing apparatus 1 in the first embodiment. The information processing apparatus 1 includes a landmark storage unit 101, a first calculator 103, a first function storage unit 105, a segment data storage unit 107, a second calculator 109, a second function storage unit 111, a division unit 113, a data storage unit 115, and an output unit 117.

The first calculator 103 performs processing based on data stored in the landmark storage unit 101, and stores a result of the processing in the first function storage unit 105. The second calculator 109 performs processing based on data stored in the segment data storage unit 107, and stores a result of the processing in the second function storage unit 111. The division unit 113 performs processing based on data stored in the first function storage unit 105 and data stored in the second function storage unit 111, and stores a result of the processing in the data storage unit 115. The output unit 117 outputs data stored in the data storage unit 115.

Figure 2:
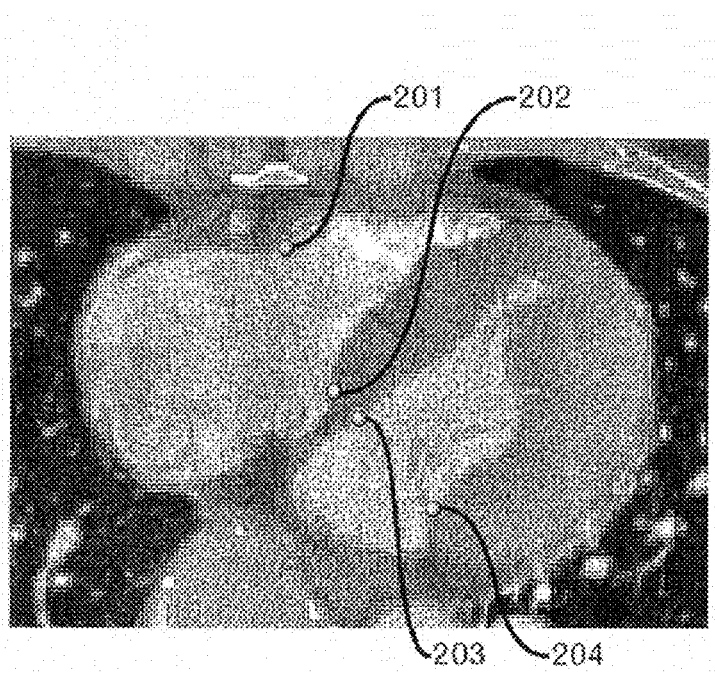
FIG. 2 is a diagram for explaining landmarks.
Figure 3:
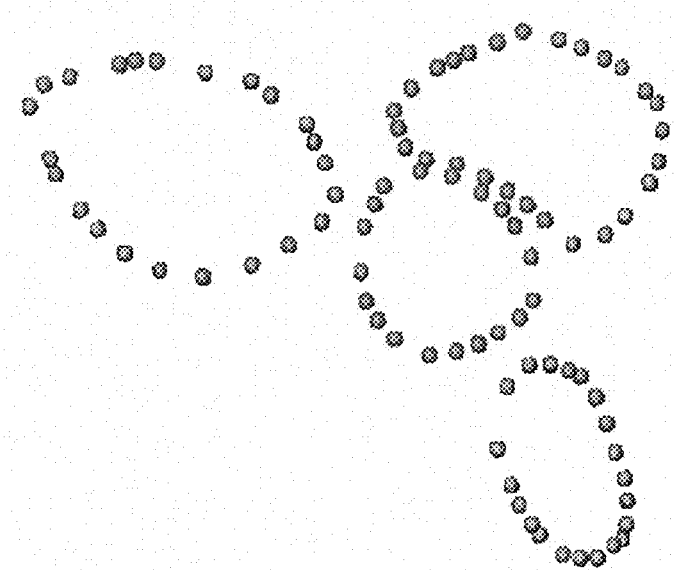
FIG. 3 is a diagram for explaining landmarks.

FIG. 2 illustrates an example of landmarks deployed on a medical image. FIG. 2 illustrates a medical image of a ventricle, and landmarks 201 to 204 are deployed on two valve annuluses. The cut surface is almost perpendicular to a surface that passes through the valve annuluses. An interpreter of a radiogram deploys the landmarks as illustrated in FIG. 2 for plural layers of medical images. Then, when the landmarks deployed on plural layers of medical images are extracted, they are represented as illustrated in FIG. 3. In an example of FIG. 3, landmarks deployed for each of a pulmonary valve, an aortic valve, a mitral valve and a tricuspid valve. The landmark storage unit 101 stores positional information of the deployed landmarks (for example, information representing positions on a three-dimensional structured grid).

Figure 4:
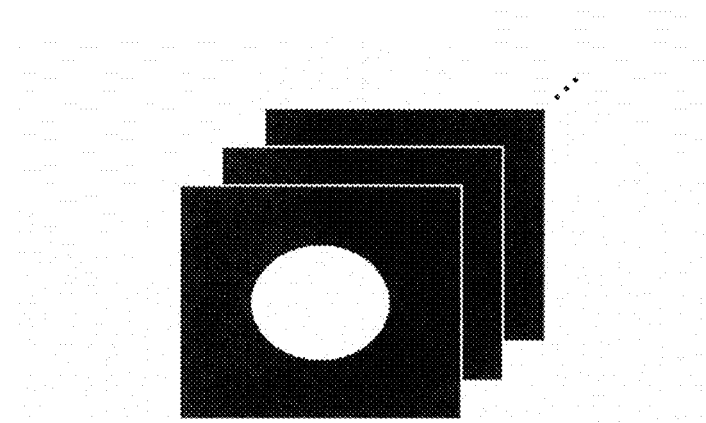
FIG. 4 is a diagram for explaining segment data.

Segment data stored in the segment data storage unit 107 is data of the three-dimensional structured grid. The three-dimensional structured grid is a uniform grid of rectangular prisms. A label value "1" is given to a grid point that is located in the inside of a boundary surface of an object, and a label value "0" is given to a grid point that is located in the outside of the boundary surface of the object. Segment data is generated from medical images as illustrated in FIG. 4, in which an area corresponding to the inside of the boundary surface of the object and an area corresponding to the outside of the boundary surface of the object are designated. In an example of FIG. 4, the area corresponding to the inside of the boundary surface of the object is represented in white, and the area corresponding to the outside of the boundary surface of the object is represented in black. The designation of the areas is called segmentation, and the designation is conducted by the interpreter of a radiogram.

Figure 5:
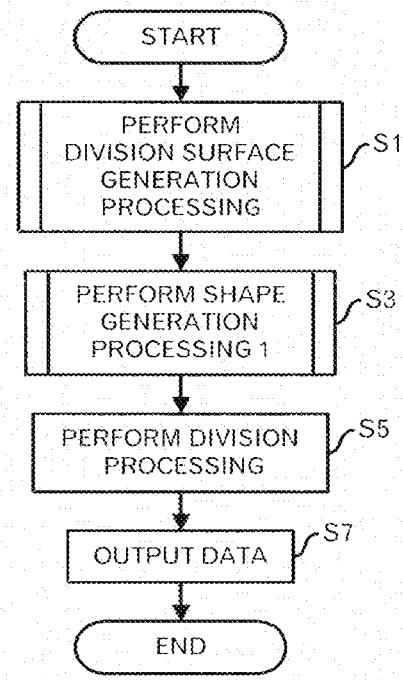
FIG. 5 is a diagram depicting main processing flow in the first embodiment.
Figure 6:
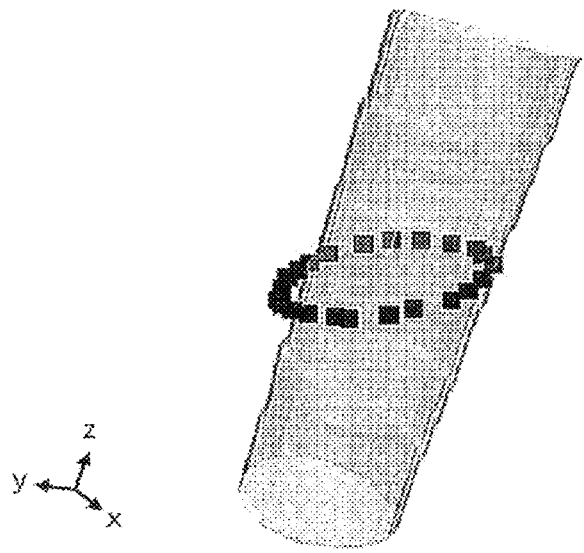
FIG. 6 is a diagram depicting a target object in the first embodiment and landmarks.

Next, by using FIGS. 5 to 15, processing performed by the information processing apparatus 1 in the first embodiment is explained. In order to make the explanation easy to be understood, in the first embodiment, an object and landmarks as illustrated in FIG. 6 is used for the explanation as an example. In FIG. 6, square diagrams represent the landmarks, and the landmarks are deployed annularly. The shape of the object is a cylinder shape, and a long axis direction of the object corresponds to the z-axis direction.

Firstly, the first calculator 103 of the information processing apparatus 1 performs division surface generation processing (FIG. 5: step S1). The division surface generation processing is explained by using FIGS. 7 and 8.

Figure 7:
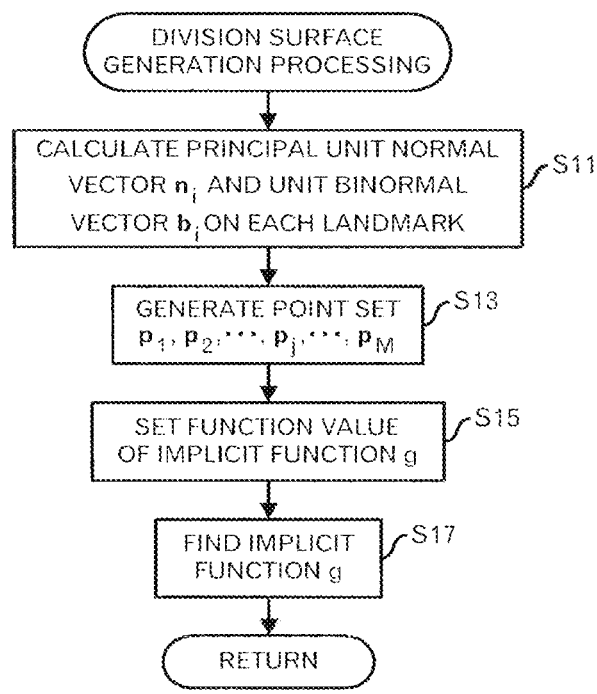
FIG. 7 is a diagram depicting processing flow of division surface generation processing.

The first calculator 103 calculates, based on positional information of landmarks $x_1, x_2, \ldots, x_i, \ldots, x_N$ stored in the landmark storage unit 101, a principal unit normal vector $n_i$ and a unit binormal vector $b_i$ at each of the landmark (FIG. 7: step S11). Here, N is the number of the landmarks.

The following is the detail of the calculation in the step S1. First, $x_{cl}$ is calculated as follows:

$$x_{cl} = \frac{1}{N}\sum_{i=1}^{N} x_i$$

Next, $s_i$ are calculated based on $x_i$ as follows:

$$s_i = \begin{cases} \frac{x_1 - x_{N-1}}{|x_1 - x_{N-1}|} & i = N \\ \frac{x_2 - x_N}{|x_2 - x_N|} & i = 1 \\ \frac{x_{i+1} - x_{i-1}}{|x_{i+1} - x_{i-1}|} & \text{otherwise} \end{cases}$$

Next, $n_i$ tilde are calculated based on $s_i$ as follows:

$$\tilde{n}_i = \begin{cases} \frac{s_1 - s_{N-1}}{|s_1 - s_{N-1}|} & i = N \\ \frac{s_2 - s_N}{|s_2 - s_N|} & i = 1 \\ \frac{s_{i+1} - s_{i-1}}{|s_{i+1} - s_{i-1}|} & \text{otherwise} \end{cases}$$

This calculation is performed in order to make directions of the principal normals the same. Next, $n_i$ hat are calculated based on $n_i$ tilde as follows:

$$\hat{n}_i = \begin{cases} \tilde{n}_i & \tilde{n}_i \cdot (x_i - x_{cl}) \geq 0 \\ -\tilde{n}_i & \tilde{n}_i \cdot (x_i - x_{cl}) < 0 \end{cases}$$

This calculation is performed in order to suppress fluctuation of the principal normal vectors. Next, principal unit normal vectors $n_i$ are calculated based on $n_i$ hat as follows:

$$n_i = \begin{cases} \dfrac{\hat{n}_1 + 2\hat{n}_N + \hat{n}_{N-1}}{|\hat{n}_1 + 2\hat{n}_N + \hat{n}_{N-1}|} & i = N \\ \dfrac{\hat{n}_2 + 2\hat{n}_1 + \hat{n}_N}{|\hat{n}_2 + 2\hat{n}_1 + \hat{n}_N|} & i = 1 \\ \dfrac{\hat{n}_{i+1} + 2\hat{n}_i + \hat{n}_{i-1}}{|\hat{n}_{i+1} + 2\hat{n}_i + \hat{n}_{i-1}|} & \text{otherwise} \end{cases}$$

Next, unit binormal vectors $b_i$ are calculated based on principal unit normal vectors $n_i$ as follows:

$$b_i = \begin{cases} \dfrac{n_1 - n_{N-1}}{|n_1 - n_{N-1}|} & i = N \\ \dfrac{n_2 - n_N}{|n_2 - n_N|} & i = 1 \\ \dfrac{n_{i+1} - n_{i-1}}{|n_{i+1} - n_{i-1}|} & \text{otherwise} \end{cases}$$

Then, the first calculator 103 generates a point set $p_1$, $p_2$, ..., $p_j$, ..., $p_M$ (step S13). In the step S13, the following point set is generated assuming that M=3N.

$$p_j = \begin{cases} x_j & j = 1, \ldots, N \\ x_{j-N} + \varepsilon_b b_{j-N} & j = N+1, \ldots, 2N \\ x_{j-2N} - \varepsilon_b b_{j-2N} & j = 2N+1, \ldots, 3N \end{cases}$$

In other words, the generated point set includes the landmarks, points that correspond to the landmarks shifted in a positive direction of the binormals by $\varepsilon_b$, and points that correspond to the landmarks shifted in a negative direction of the binormals by $\varepsilon_b$. $\varepsilon_b$ is a constant number, and a number sufficiently less than a distance between the landmarks is employed. In this embodiment, assume $\varepsilon_b = 1.0$.

The first calculator 103 sets a function value of an implicit function g (step S15). More specifically, the function value is set as follows. By this setting, it becomes possible to suppress occurrence of concavity and convexity on a surface formed by a point set that makes the value of the implicit function g equal to 0.

$$g_j = \begin{cases} 0 & j = 1, \ldots, N \\ \varepsilon_b & j = N+1, \ldots, 2N \\ -\varepsilon_b & j = 2N+1, \ldots, 3N \end{cases}$$

The first calculator 103 finds the implicit function g so that the function value becomes the value set in the step S15 (step S17), and stores data of the implicit function g in the first function storage unit 105. Then the processing returns to the calling-source processing.

In the step S17, by using TPS (Thin Plate Spline), $\alpha_j$, $\beta_0$, $\beta_1$, $\beta_2$, and $\beta_3$ are determined so that the following expressions are satisfied. Here, a basis function is $\varphi_j(x) = -|x - p_j|$.

$$g(x) = \sum_{j=1}^{M} \alpha_j \phi_j(x) + \beta_0 + \beta_1 x + \beta_2 y + \beta_3 z$$

$$g(p_j) = g_j = \sum_{j=1}^{M} \alpha_j \phi_j(p_j) + \beta_0 + \beta_1 p_{j,x} + \beta_2 p_{j,y} + \beta_3 p_{j,z} \quad (1)$$

$$\sum_{j=1}^{M} \alpha_j = 0 \quad (2)$$

$$\sum_{j=1}^{M} \alpha_j p_j = 0 \quad (3)$$

Here, simultaneous linear equations including expression (1), expression (2), and expression (3) are solved by a common solution (for example, Gaussian elimination or LU decomposition) to determine $\alpha_j$, $\beta_0$, $\beta_1$, $\beta_2$, and $\beta_3$. And assume $x = (x, y, z)$ and $p_j = (p_{j,x}, p_{j,y}, p_{j,z})$.

Figure 8:
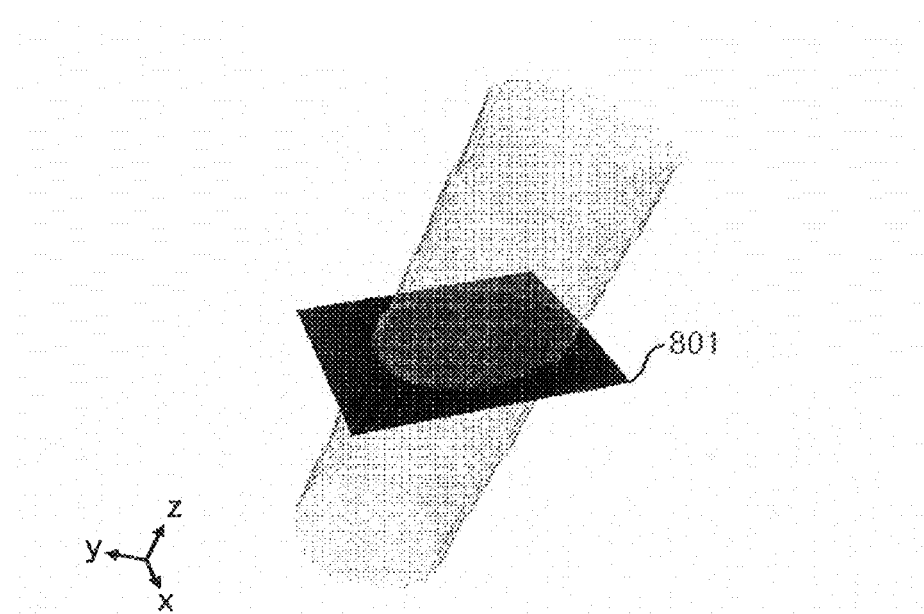
FIG. 8 is a diagram for explaining a division surface.

FIG. 8 illustrates a surface formed by the point set that makes the value of the implicit function g equal to 0 (hereinafter, referred to as a division surface). In FIG. 8, the division surface 801 is represented in black. The division surface 801 passes through the landmarks $x_1$, $x_2$, ..., $x_i$, ..., $x_N$. Values of the implicit function g are positive in a positive direction of binormals for the landmarks, and values of the implicit function g are negative in a negative direction of the binormals for the landmarks. Here, in order to make a relationship between the object and the division surface easy to be understood, a part of the division surface is illustrated.

Returning to the explanation of FIG. 5, the second calculator 109 performs shape generation processing in the first embodiment (step S3). The shape generation processing in the first embodiment is explained using FIGS. 9 to 14.

Figure 9:
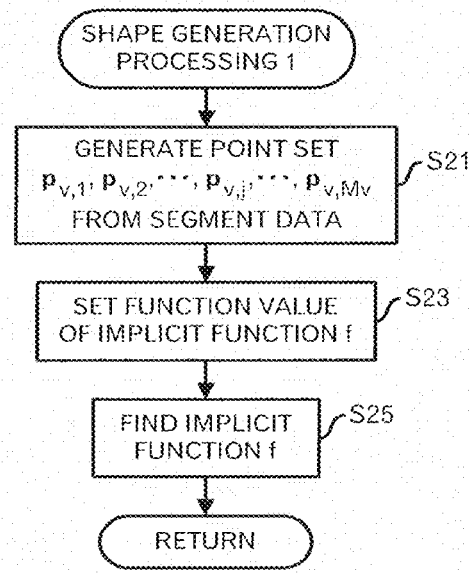
FIG. 9 is a diagram depicting processing flow of shape generation processing in the first embodiment.

Firstly, the second calculator 109 generates a point set $p_{v,1}$, $p_{v,2}$, ..., $p_{v,j}$, ..., $p_{v,Mv}$ from the segment data stored in the segment data storage unit 107 (FIG. 9: step S21).

In the step S21, the point set $p_{v,1}$, $p_{v,2}$, ..., $p_{v,j}$, ..., $p_{v,Mv}$ is generated as follows. Subscript v represents that the point set corresponds to a boundary of the object.

At first, of grid points that are located inside the boundary surface (in other words, grid points whose label values are 0), grid points whose at least one of adjacent grid points is located outside the boundary surface (in other words, grid points whose label value are 1) are set as inner boundary points. Here, "adjacent grid points" are 6 points that include 2 points separated from a target grid point by $1d_x$ ($d_x$ is a distance between grid points in the x-axis direction) in the x-direction, 2 points separated from the target grid point by $1d_y$ ($d_y$ is a distance between grid points in the y-axis direction) in the y-direction, and 2 points separated from the target grid point by $1d_z$ ($d_z$ is a distance between grid points in the z-axis direction) in the z-direction. However, the number of the adjacent grid points is less than 6 if the target grid point is located on an edge of a space.

Figure 10:
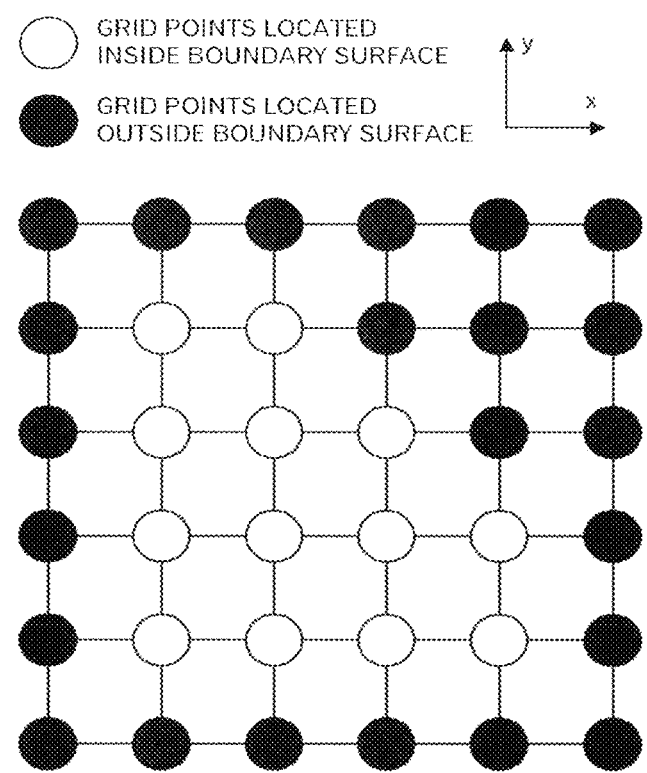
FIG. 10 is a diagram for explaining inner boundary points and outer boundary points.
Figure 11:
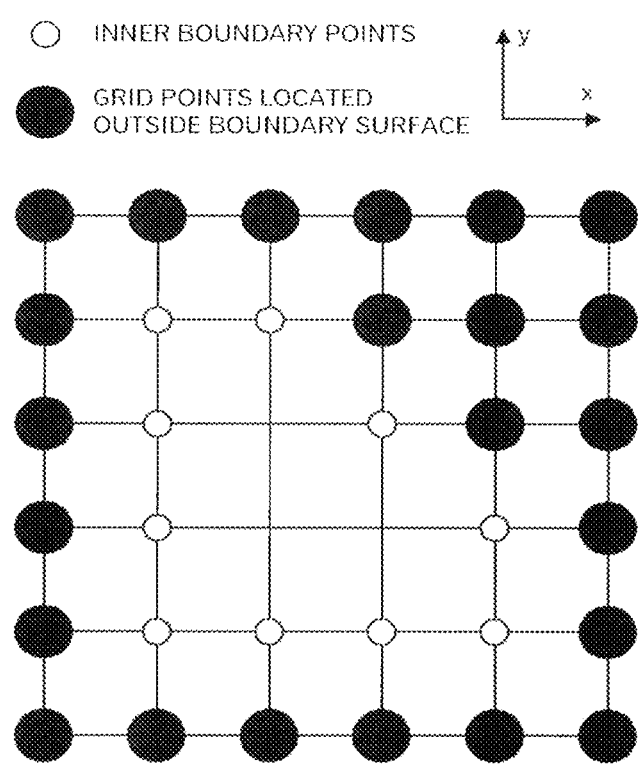
FIG. 11 is a diagram for explaining inner boundary points and outer boundary points.

For example, segment data in a certain xy-plane is in a state as illustrated in FIG. 10. In FIG. 10, grid points located inside the boundary surface are represented by white circles, and grid points located outside the boundary surface are represented by black circles. In this case, inner boundary points are set, for example, as illustrated in FIG. 11. In FIG. 11, the inner boundary points are represented by white circles, and grid points located outside the boundary surface are represented by black circles. Here, the white circles that represent the inner boundary points are smaller than the white circles that represent the grid points located inside the boundary surface.

Figure 12:
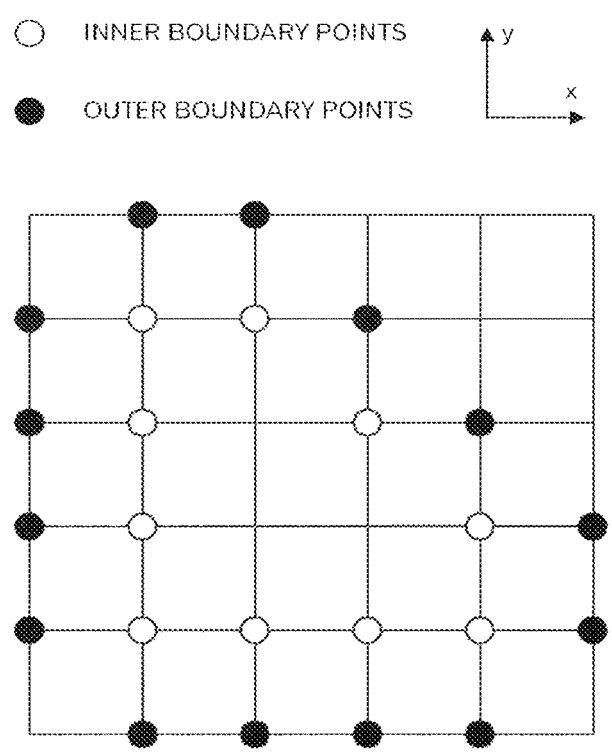
FIG. 12 is a diagram for explaining inner boundary points and outer boundary points.

Next, of the grid points located outside the boundary surface, grid points whose at least one of adjacent grid points is an inner boundary point are set as outer boundary points. For example, in a state as illustrated in FIG. 11, outer boundary points are set, for example, as illustrated in FIG. 12. In FIG. 12, the inner boundary points are represented by white circles, and the outer boundary points are represented by black circles. Here, the black circles that represent the outer boundary points are smaller than the black circles that represent the grid points located outside the boundary surface.

Figure 13:
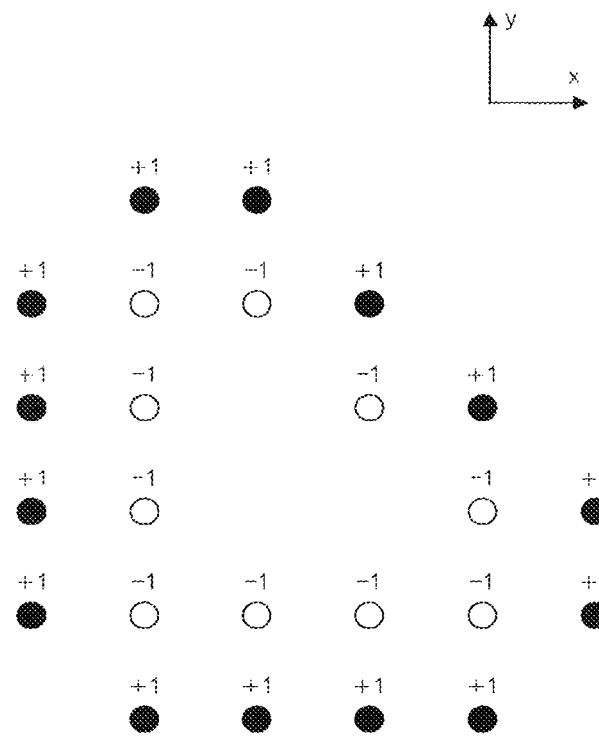
FIG. 13 is a diagram for explaining inner boundary points and outer boundary points.

Next, values of the inner boundary points are set to −1, and values of the outer boundary points are set to +1. For example, in a state as illustrated in FIG. 12, values are set as illustrated in FIG. 13.

Namely, points included in the point set $p_{v,1}, p_{v,2}, \ldots, p_{v,j}, \ldots, p_{v,M_v}$ correspond to inner boundary points or outer boundary points.

Returning to the explanation of FIG. 9, the second calculator 109 sets a function value of an implicit function f (step S23). More specifically, the function value is set as follows:

$$f(p_{v,j}) = f_j = \begin{cases} 1 & \text{when } p_{v,j} \text{ is an outer boundary point} \\ -1 & \text{when } p_{v,j} \text{ is an inner boundary point} \end{cases}$$

The first calculator 103 finds the implicit function f so that the function value becomes the value set in the step S23 (step S25), and stores data of the implicit function f in the second function storage unit 111. Then the processing returns to the calling-source processing.

In the step S23, the implicit function f is found using TPS. When it takes time to find the implicit function f using TPS, the implicit function f may be found by a method, for example, described in the non-patent document 1. The disclosure of the non-patent document 1 is incorporated herein by reference.

Figure 14:
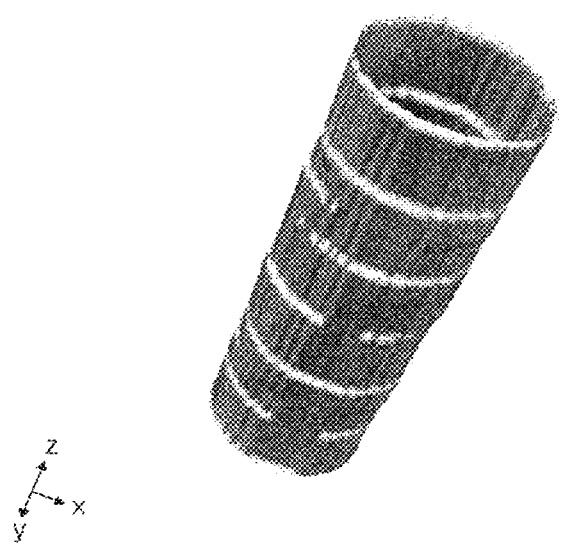
FIG. 14 is a diagram depicting a boundary of the object.

FIG. 14 illustrates a boundary formed by a point set that makes the value of the implicit function f equal to 0 (hereinafter, referred to as a 0 isosurface of the implicit function f). In FIG. 14, values of the implicit function f are negative inside the boundary (in other words, inside the cylinder), and values of the implicit function f are positive outside the boundary (in other words, outside the cylinder).

Returning to the explanation of FIG. 5, the division unit 113 performs division processing based on data of the implicit function g stored in the first function storage unit 105 and data of the implicit function f stored in the second function storage unit 111 (step S5), and stores volume data representing a divided shape in the data storage unit 115.

The division processing is processing to divide a shape represented by the 0 isosurface of the implicit function f by a 0 isosurface of the implicit function g. For example, a point set that satisfies the implicit function f=0 and the implicit function g>0 is found in the division processing, and volume data for the point set is stored in the data storage unit 115.

When the volume data is generated by the same structured grid as the segment data, firstly, a structured grid is generated using the number of grid points, voxel sizes, and origin coordinates of the segment data. Then, for each grid point, the value is set to −1 when the grid point satisfies the implicit function g>0 and the implicit function f>0, and the value is set to +1 when the grid point satisfies the implicit function g>0 and does not satisfy the implicit function f>0. Thus, two-valued volume data is generated. Moreover, mesh data may be generated by attaching mesh to the volume data by marching cubes method for example.

Figure 15:
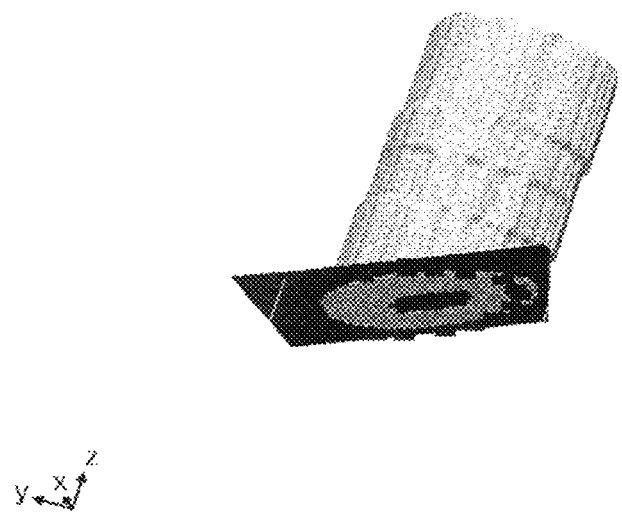
FIG. 15 is a diagram depicting the object divided by the division surface.

The output unit 117 outputs the volume data stored in the data storage unit 115 to a display device (step S7). FIG. 15 illustrates an example of displayed volume data and division surface. As illustrated in FIG. 15, the object is divided by the division surface that passes through the landmarks, and a part of the object, which satisfies the implicit function g>0, is outputted.

When a basis function of the implicit function g, and a basis function of the implicit function f, $\alpha_j, \beta_0, \beta_1, \beta_2, \beta_3$ and a composition method of the implicit function g and the implicit function f are outputted, a user himself can reproduce a display illustrated in FIG. 15. By doing this, there is an advantage that the user change the number of grid points arbitrarily when the volume data is outputted. Moreover, if the number of grid points is decreased, the size of stored volume data becomes smaller.

By performing processing described above, it becomes possible to divide an object in a part that has an annular structure. And, when this embodiment is applied to valve annulus, a boundary surface that divides a ventricle and a part other than the ventricle can be generated, and it becomes easy to extract only the ventricle or the part other than the ventricle. Thus, it becomes easy to separately set parameters for the ventricle and parameters for the part other than the ventricle. Moreover, when compared to a method to generate the ventricle or the part other than the ventricle separately and combine them, the reliability of the simulator becomes higher because a shape of combining site is analogous to an actual shape.

Embodiment 2

In the second embodiment, an example in which a shape of an object is modified according to landmarks deployed annularly is explained.

Figure 16:
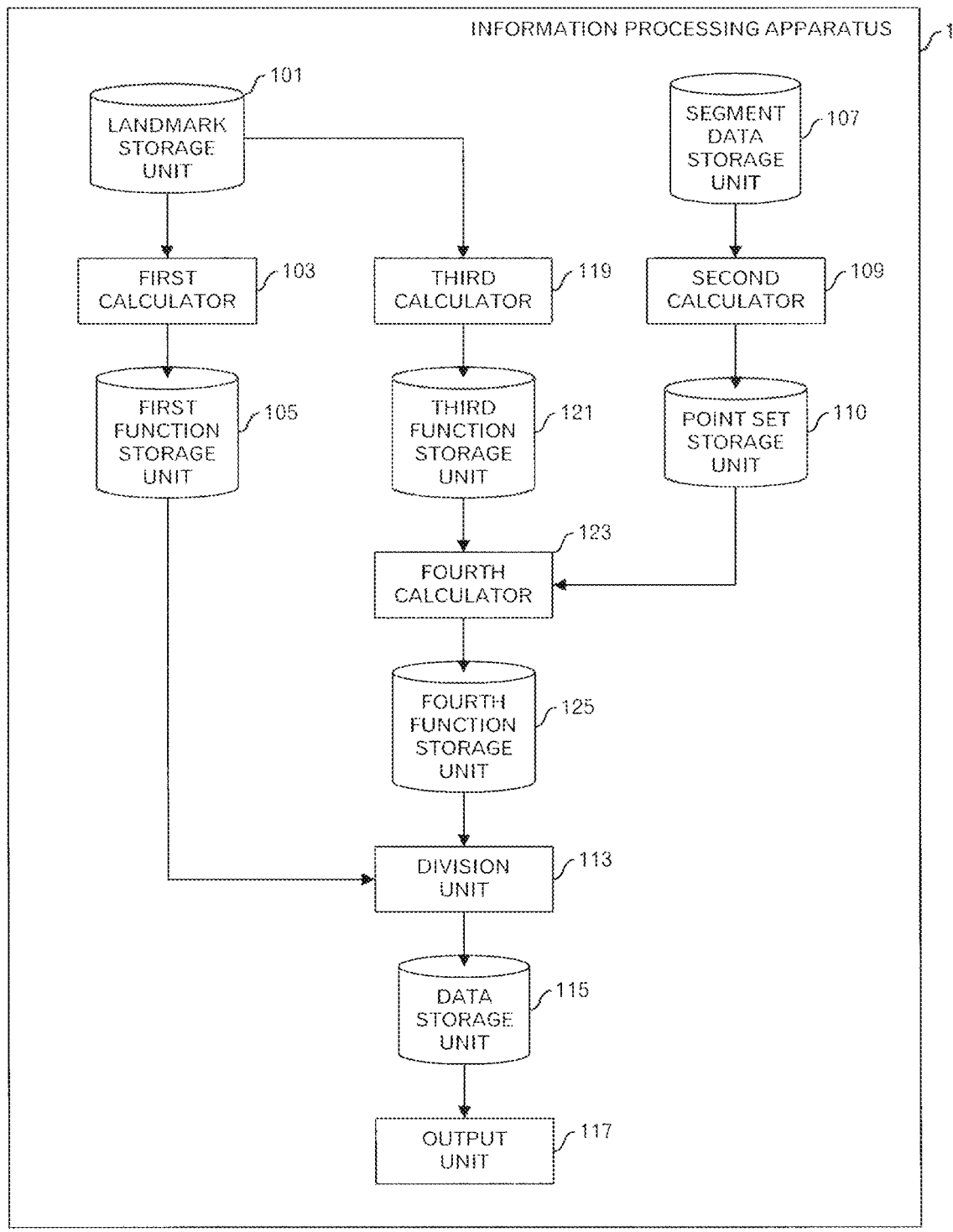
FIG. 16 is a diagram depicting a functional block diagram of the information processing apparatus in a second embodiment.

FIG. 16 illustrates a functional block diagram of the information processing apparatus 1 in the second embodiment. The information processing apparatus 1 includes the landmark storage unit 101, the first calculator 103, the first function storage unit 105, the segment data storage unit 107, the second calculator 109, a point set storage unit 110, a third calculator 119, a third function storage unit 121, a fourth calculator 123, a fourth function storage unit 125, the division unit 113, the data storage unit 115, and an output unit 117.

The first calculator 103 performs processing based on data stored in the landmark storage unit 101, and stores a result of the processing in the first function storage unit 105. The second calculator 109 performs processing based on data stored in the segment data storage unit 107, and stores a result of the processing in the point set storage unit 110. The third calculator 119 performs processing based on data stored in the landmark storage unit 101, and stores a result of the processing in the third function storage unit 121. The fourth calculator 123 performs processing based on data stored in the point set storage unit 110 and data stored in the third function storage unit 121, and stores a result of the processing in the fourth function storage unit 125. The division unit 113 performs processing based on data stored in the first function storage unit 105 and data stored in the fourth function storage unit 125, and stores a result of the processing in the data storage unit 115. The output unit 117 outputs data stored in the data storage unit 115.

Next, by using FIGS. 17 to 24, processing performed by the information processing apparatus 1 in the second embodiment is explained. Also in the second embodiment, an object and landmarks as illustrated in FIG. 6 is used for the explanation as an example.

Figure 17:
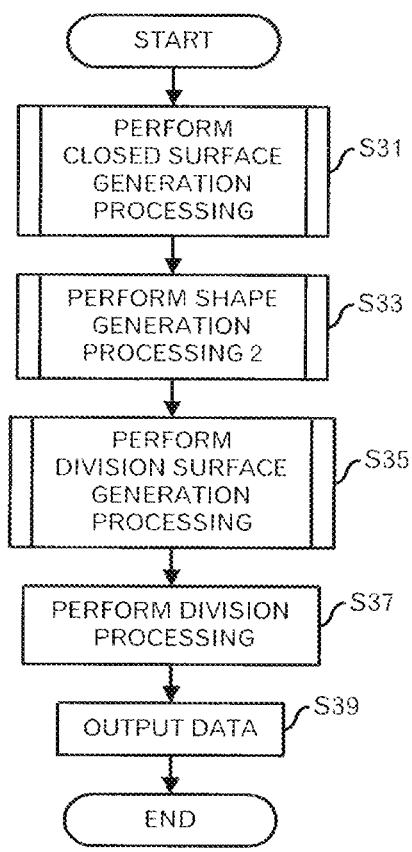
FIG. 17 is a diagram depicting main processing flow in the second embodiment.

Firstly, the third calculator 119 performs closed surface generation processing (FIG. 17: step S31). The closed surface generation processing is explained by using FIGS. 18 to 24.

Figure 18:
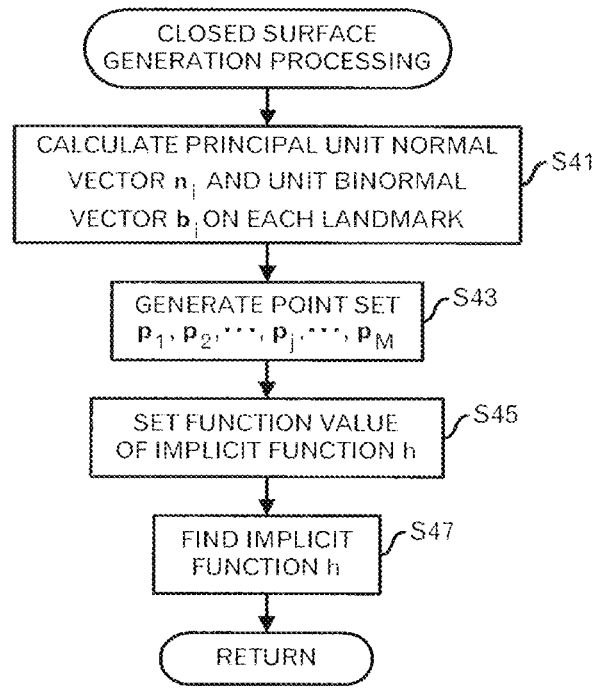
FIG. 18 is a diagram depicting processing flow of closed surface generation processing.

The third calculator 119 calculates, based on positional information of landmarks $x_1, x_2, \ldots, x_i, \ldots, x_N$ stored in the landmark storage unit 101, a principal unit normal vector $n_i$ and a unit binormal vector $b_i$ at each of the landmark (FIG. 18: step S41). This processing is the same as the step S11 in the first embodiment, and the explanation is omitted.

Then, the third calculator 119 generates a point set $p_1, p_2, \ldots, p_j, \ldots, p_M$ (step S43). In the step S43, the following point set is generated assuming that M=5N.

$$p_j = \begin{cases} x_j + Dn_j & j = 1, \ldots, N \\ x_{j-N} + (D + \varepsilon_b)n_{j-N} & j = N+1, \ldots, 2N \\ x_{j-2N} + (D - \varepsilon_b)n_{j-2N} & j = 2N+1, \ldots, 3N \\ x_{j-3N} + Dn_{j-3N} + 7\varepsilon_b b_{j-3N} & j = 3N+1, \ldots, 4N \\ x_{j-4N} + Dn_{j-4N} - 7\varepsilon_b b_{j-4N} & j = 4N+1, \ldots, 5N \end{cases}$$

In other words, the generated point set includes points that correspond to the landmarks shifted in a positive direction of the normals by D, points that correspond to the landmarks shifted in a positive direction of the normals by (D+$\varepsilon_b$), points that correspond to the landmarks shifted in a positive direction of the normals by (D−$\varepsilon_b$), points that correspond to the landmarks shifted in a positive direction of the normals by D and shifted in a positive direction of the binormals by 7$\varepsilon_b$, and points that correspond to the landmarks shifted in a positive direction of the normals by D and shifted in a negative direction of the binormals by 7$\varepsilon_b$. $\varepsilon_b$ is a constant number, and a number sufficiently less than a distance between the landmarks is employed. In this embodiment, assume $\varepsilon_b$=1.0. It is favorable that D is set so that a closed surface contains the landmarks and a boundary on a surface that passes through the landmarks. In this embodiment, assume D=5$\varepsilon_b$.

The third calculator 119 sets a function value of an implicit function h (step S45). More specifically, the function value is set as follows. By this setting, a point set that satisfies h=0 forms the closed surface that contains the landmarks deployed annularly.

$$h_j = \begin{cases} 0 & j = 1, \ldots, N \\ \varepsilon_b & j = N+1, \ldots, 2N \\ -\varepsilon_b & j = 2N+1, \ldots, 3N \\ 3\varepsilon_b & j = 3N+1, \ldots, 4N \\ 3\varepsilon_b & j = 4N+1, \ldots, 5N \end{cases}$$

The third calculator 119 finds the implicit function h so that the function value becomes the value set in the step S45 (step S47), and stores data of the implicit function h in the third function storage unit 121. Then the processing returns to the calling-source processing. Also in the step S47, the implicit function h is found using TPS. The basic idea is the same as the processing in the step S17, the explanation is omitted.

Figure 19:
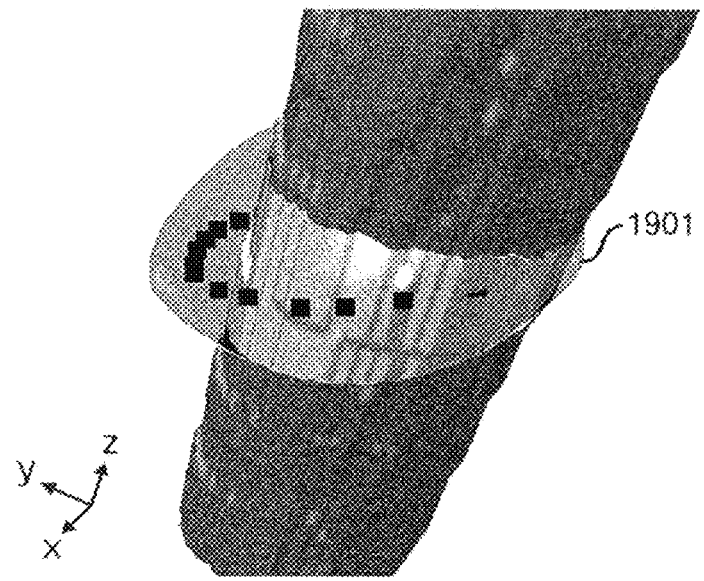
FIG. 19 is a diagram for explain a closed surface.
Figure 20:
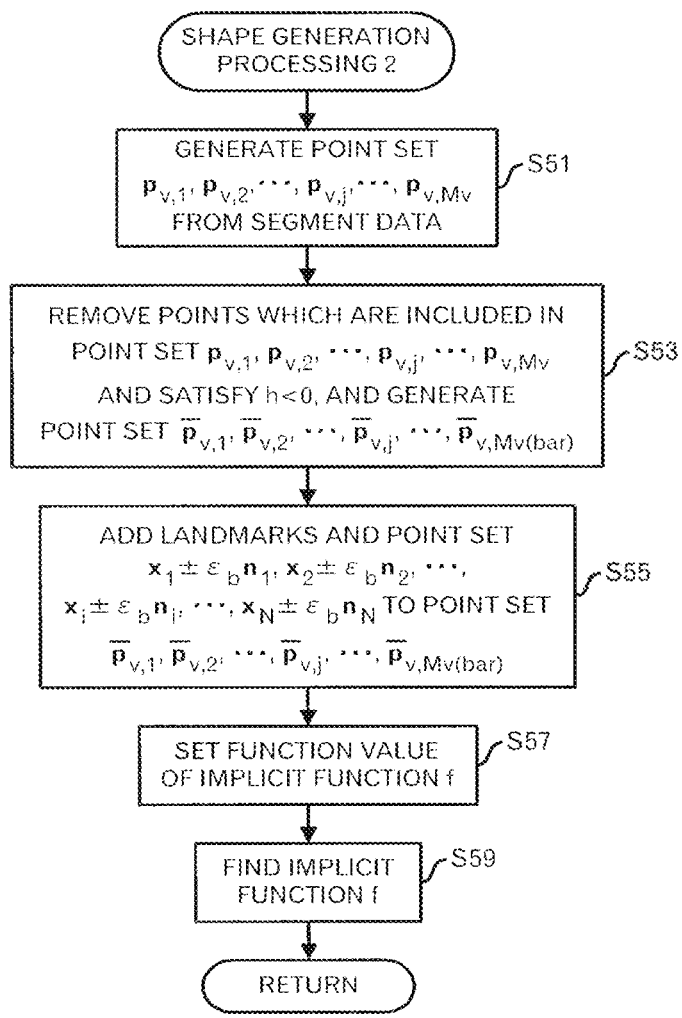
FIG. 20 is a diagram depicting processing flow of shape generation processing in the second embodiment.

FIG. 19 illustrates a surface formed by a point set that makes the implicit function h equal to 0 (hereinafter, referred to as a 0 isosurface of the implicit function h). In FIG. 19, square diagrams represent the landmarks, and the 0 isosurface of the implicit function h 1901 is a closed surface whose shape is an ellipsoid. The 0 isosurface of the implicit function h 1901 contains the landmarks. Values of the implicit function h are negative inside the closed surface, and values of the implicit function h are positive outside the closed surface.

Returning to the explanation of FIG. 17, the second calculator 109 and the fourth calculator 123 perform shape generation processing in the second embodiment (step S33). The shape generation processing in the second embodiment is explained using FIGS. 20 to 22.

Firstly, the second calculator 109 generates a point set $p_{v,1}, p_{v,2}, \ldots, p_{v,j}, \ldots, p_{v,Mv}$ from the segment data stored in the segment data storage unit 107 (FIG. 20: step S51), stores it in the point set storage unit 110.

The point set generated in the step S51 is the same as the point set generated in the step S21. In other words, points included in the point set $p_{v,1}, p_{v,2}, \ldots, p_{v,j}, \ldots, p_{v,Mv}$ correspond to inner boundary points or outer boundary points.

The fourth calculator 123 removes, of the points included in the point set $p_{v,1}, p_{v,2}, \ldots, p_{v,j}, \ldots, p_{v,Mv}$ points that satisfy h<0, and generates a point set p(bar)$_{v,1}$, p(bar)$_{v,2}$, ..., p(bar)$_{v,j}$, ..., p(bar)$_{v,Mv(bar)}$ (step S53). The points that satisfy h<0 correspond to points that exist inside the 0 isosurface of the implicit function h. p(bar) represents a bar "-" is attached to p. Moreover, $_{v,Mv(bar)}$ represents a bar "-" is attached to a subscript M and v.

The fourth calculator 123 adds the landmarks $x_1, x_2, \ldots, x_i, \ldots, x_N$ and the point set $x_1 \pm \varepsilon_b n_1, x_2 \pm \varepsilon_b n_2, \ldots, x_i \pm \varepsilon_b n_i, \ldots, x_N \pm \varepsilon_b n_N$ to the generated point set p(bar)$_{v,1}$, p(bar)$_{v,2}$, ..., p(bar)$_{v,j}$, ..., p(bar)$_{v,Mv(bar)}$ (step S55).

Figure 21:
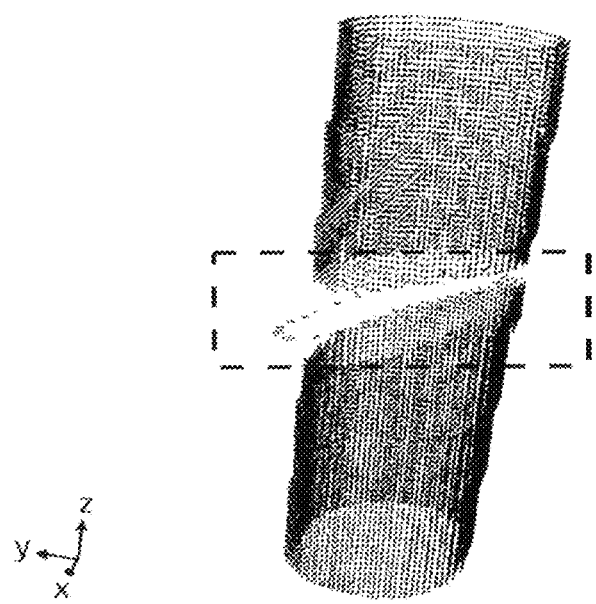
FIG. 21 is a diagram depicting a point set representing a boundary of the object.

FIG. 21 illustrates an example of the generated point set. In the vicinity of the landmarks (a part illustrated by a dotted line in FIG. 21), points which are included in the point set representing the boundary of the object and are located inside the closed surface are removed, and the landmarks are added. Moreover, points corresponding to the landmarks shifted in a positive direction of the normals by $\varepsilon_b$ and points corresponding to the landmarks shifted in a negative direction of the normals by $\varepsilon_b$ are added in order to stabilize the shape in the vicinity of the landmarks.

The fourth calculator 123 sets a function value of the implicit function f (step S57). More specifically, the function value is set as follows:

$$f(\bar{p}_{v,j}) = \begin{cases} 1 & \text{when } \bar{p}_{v,j} \text{ is an outer boundary point} \\ -1 & \text{when } \bar{p}_{v,j} \text{ is an inner boundary point} \end{cases}$$

$$f(x_j) = 0$$

$$f(x_j \pm \varepsilon_b n_j) = \pm 1$$

The fourth calculator 123 finds the implicit function f so that the function value becomes the value set in the step S57 (step S59), and stores data of the implicit function f in the fourth function storage unit 125. Then the processing returns to the calling-source processing.

In the step S59, as well as the first embodiment, the implicit function f is found by using TPS. When it takes time to find the implicit function f using TPS, the implicit function f may be found by a method, for example, described in the non-patent document 1. The disclosure of the non-patent document 1 is incorporated herein by reference.

Figure 22:
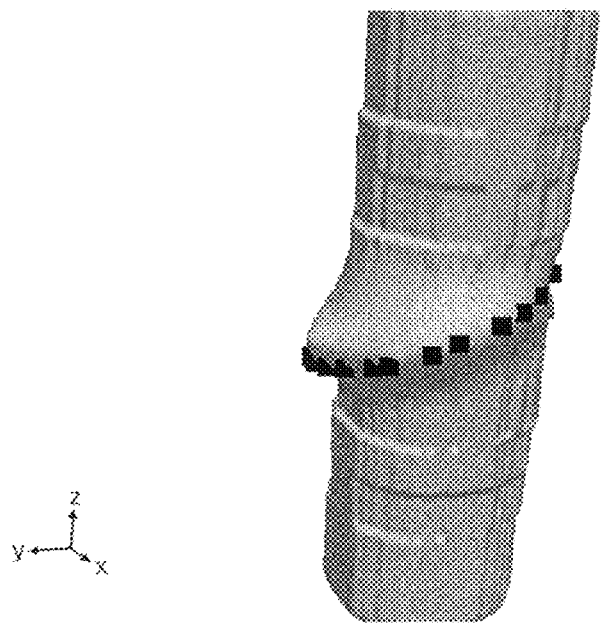
FIG. 22 is a diagram depicting the boundary of the object.

FIG. 22 illustrates a boundary formed by a point set that makes the value of the implicit function f equal to 0 (hereinafter, referred to as a 0 isosurface of the implicit function f). In FIG. 22, square diagrams represent the landmarks. Values of the implicit function f are negative inside the boundary (in other words, inside the cylinder), and values of the implicit function f are positive outside the boundary (in other words, outside the cylinder). The boundary is formed so as to pass through the landmarks because the function value is set as described above.

Figure 23:
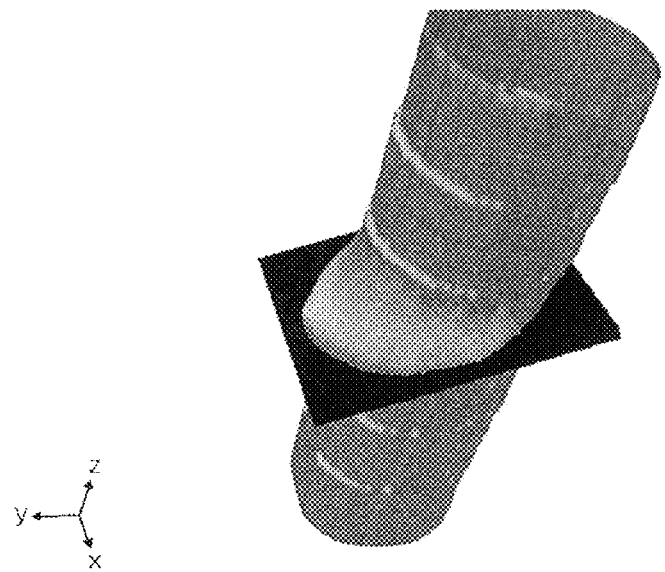
FIG. 23 is a diagram for explaining the division surface.

Returning to the explanation of FIG. 17, the first calculator 103 performs the division surface generation processing (FIG. 17: step S35). The division surface generation processing is the same as the one explained using FIGS. 7 and 8, the explanation is omitted. FIG. 23 illustrates a division surface generated by the division surface generation processing (in other words, a 0 isosurface of the implicit function g) and the 0 isosurface of the implicit function f. As illustrated in FIG. 23, the 0 isosurface of the implicit function g passes through the landmarks, and the object shape is divided by the 0 isosurface of the implicit function g.

The division unit 113 performs the division processing based on data of the implicit function g stored in the first function storage unit 105 and data of the implicit function f stored in the fourth function storage unit 125 (step S37), and stores volume data representing a divided shape in the data storage unit 115. The division processing in the step S37 corresponds to the division processing explained in the step S5, and the explanation is omitted.

Figure 24:
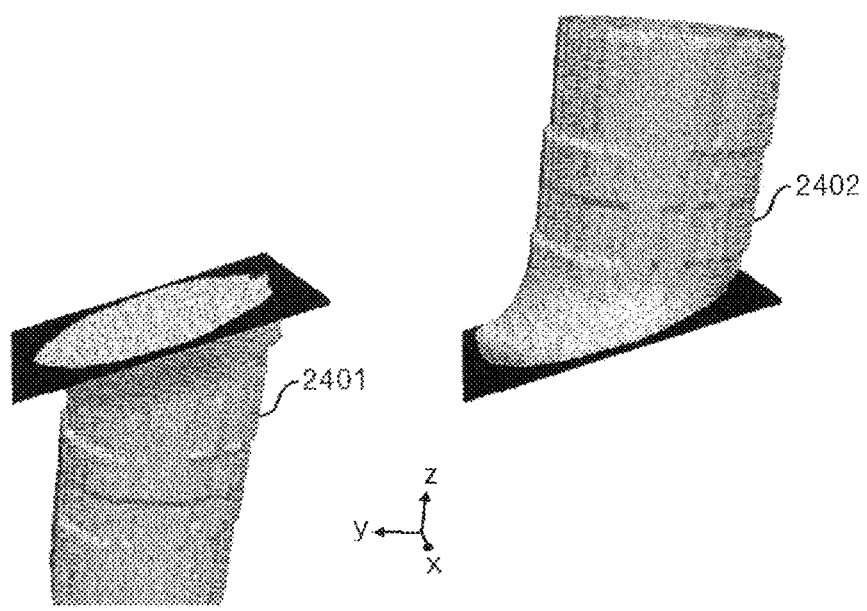
FIG. 24 is a diagram depicting a shape of the object divided by the division surface.

The output unit 117 outputs the volume data stored in the data storage unit 115 to the display device (step S39). FIG. 24 illustrates an example of displayed volume data and 0 isosurface of the implicit function g. As illustrated in FIG. 24, the object is divided by a surface that passes through the landmarks. And, in the object, a part 2401 that satisfies the implicit function g<0 and a part 2402 that satisfies the implicit function g>0 are outputted.

By performing the processing as described above, the object shape becomes analogous to the actual shape because a shape of a part that has an annular structure is corrected according to the landmarks.

Embodiment 3

In the third embodiment, an example in which a shape of a ventricle is modified based on the technique explained in the first embodiment and the technique explained in the second embodiment is explained.

Figure 25:
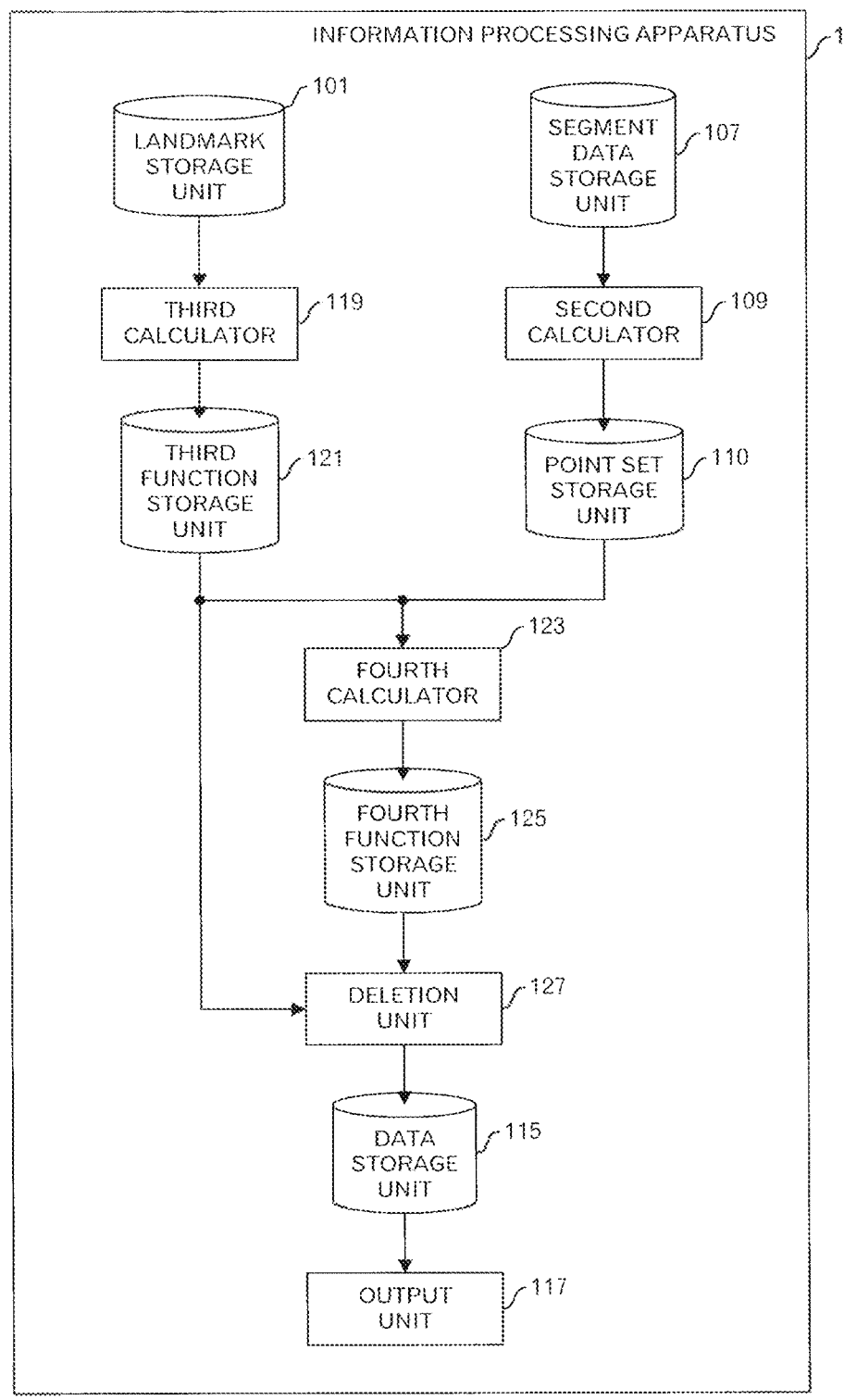
FIG. 25 is a diagram depicting a functional block diagram of the information processing apparatus in a third embodiment.

FIG. 25 illustrates a functional block diagram of the information processing apparatus 1 in the third embodiment. The information processing apparatus 1 includes the segment data storage unit 107, the second calculator 109, the point set storage unit 110, the landmark storage unit 101, the third calculator 119, the third function storage unit 121, the fourth calculator 123, the fourth function storage unit 125, a deletion unit 127, the data storage unit 115, and an output unit 117.

The second calculator 109 performs processing based on data stored in the segment data storage unit 107, and stores a result of the processing in the point set storage unit 110. The third calculator 119 performs processing based on data stored in the landmark storage unit 101, and stores a result of the processing in the third function storage unit 121. The fourth calculator 123 performs processing based on data stored in the point set storage unit 110 and data stored in the third function storage unit 121, and stores a result of the processing in the fourth function storage unit 125. The deletion unit 127 performs processing based on data stored in the fourth function storage unit 125 and data stored in the third function storage unit 121, and stores a result of the processing in the data storage unit 115. The output unit 117 outputs data stored in the data storage unit 115 to a display device or the like.

Figure 26:
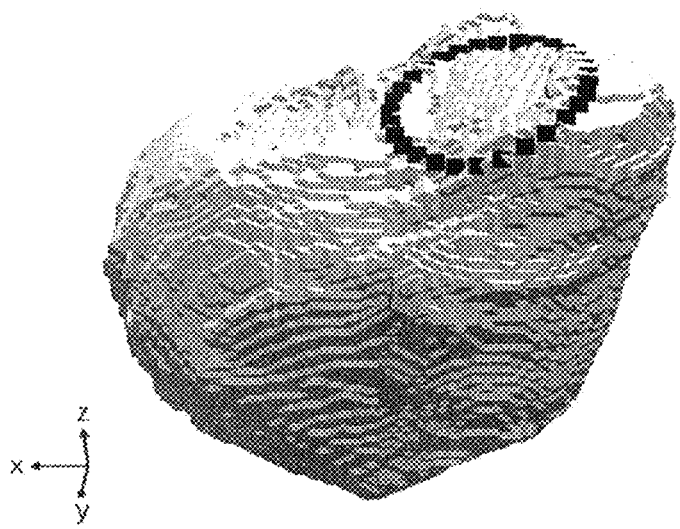
FIG. 26 is a diagram depicting landmarks deployed on a position of an valve annulus.

Next, by using FIGS. 26 to 33, processing performed by the information processing apparatus 1 in the third embodiment is explained. In the third embodiment, an object and landmarks as illustrated in FIG. 26 is used for the explanation as an example. In FIG. 26, the object is a ventricle. Square diagrams represent the landmarks, and the landmarks are deployed in the vicinity of a valve annulus. In the third embodiment, a boundary of the object is corrected according to the landmarks. Furthermore, the object shape is corrected so as to make a hole inside the valve annulus.

Figure 28:
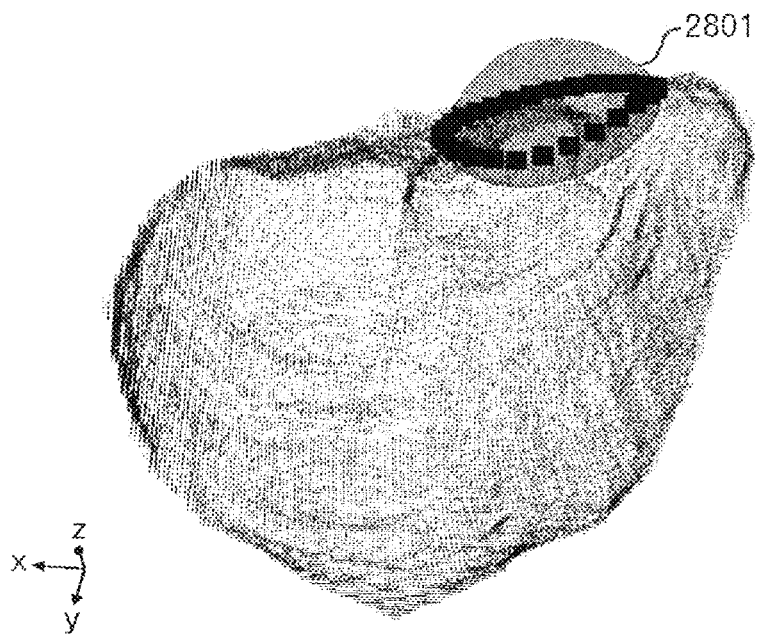
FIG. 28 is a diagram for explaining a closed surface generated by an implicit function $h_1$.
Figure 27:
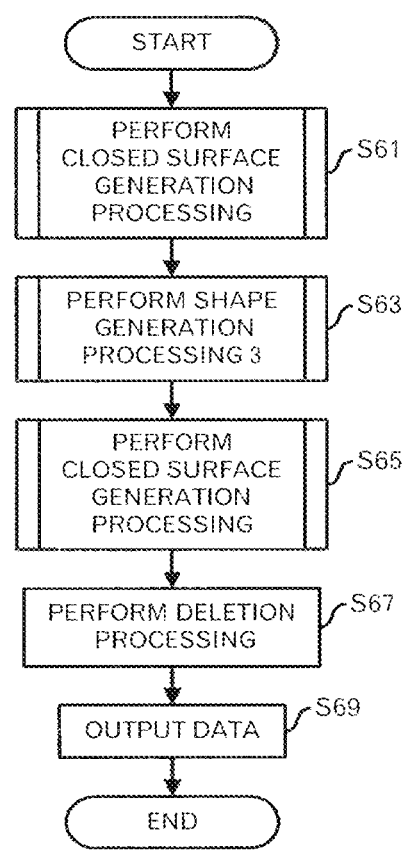
FIG. 27 is a diagram depicting main processing flow in the third embodiment.
Figure 29:
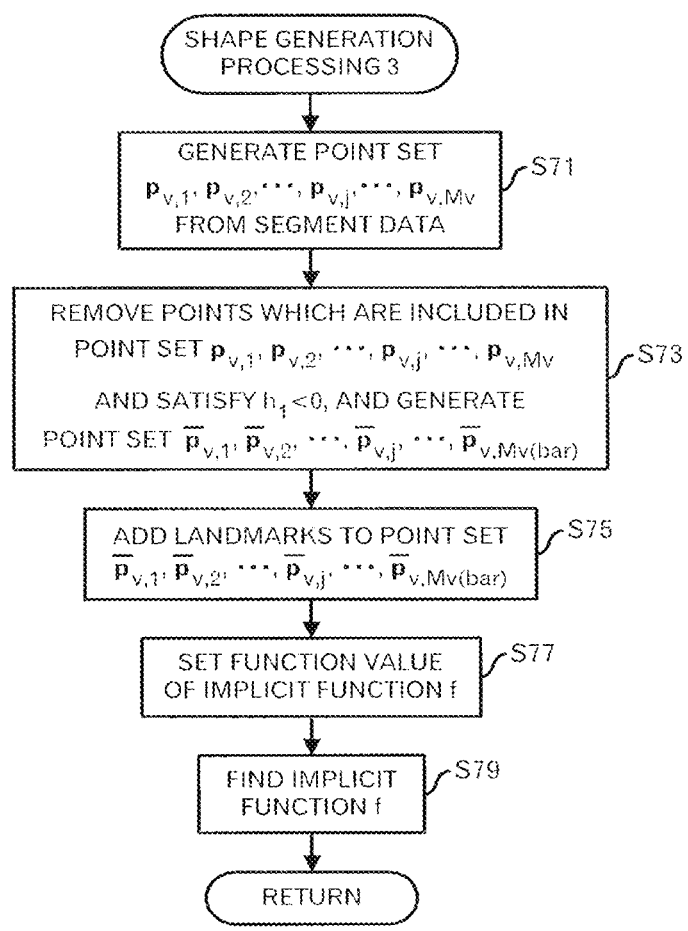
FIG. 29 is a diagram depicting processing flow of the shape generation processing in the third embodiment.

Firstly, the third calculator 119 performs the closed surface generation processing (FIG. 27: step S61). The closed surface generation processing is the same as the one explained in the second embodiment, a detailed explanation is omitted. In the step S61, for example, an implicit function $h_1$ for generating a closed surface is found assuming that $\varepsilon_b=1.0$ and $D=1.0$. FIG. 28 illustrates a surface formed by a point set that makes the value of the implicit function $h_1$ equal to 0 (hereinafter, referred to as a 0 isosurface of the implicit function $h_1$). In FIG. 28, square diagrams represent the landmarks, and the 0 isosurface of the implicit function $h_1$ 2801 corresponds to a closed surface with an ellipsoidal shape. The 0 isosurface of the implicit function $h_1$ 2801 contains the landmarks. Values of the implicit function $h_1$ are negative inside the closed surface, and values of the implicit function $h_1$ are positive outside the closed surface. Here, in order to make a positional relationship between the ventricle and the closed surface easy to be understood, a point set representing a boundary of the ventricle is illustrated in FIG. 28.

Then, the second calculator 109 and the fourth calculator 123 perform shape generation processing in the third embodiment (FIG. 27: step S63). The shape generation processing in the third embodiment is explained using FIGS. 29 to 31.

The second calculator 109 generates a point set $p_{v,1}$, $p_{v,2}$, ..., $p_{v,j}$, $p_{v,Mv}$ from the segment data stored in the segment data storage unit 107 (FIG. 29: step S71) and stores it in the point set storage unit 110.

Figure 30:
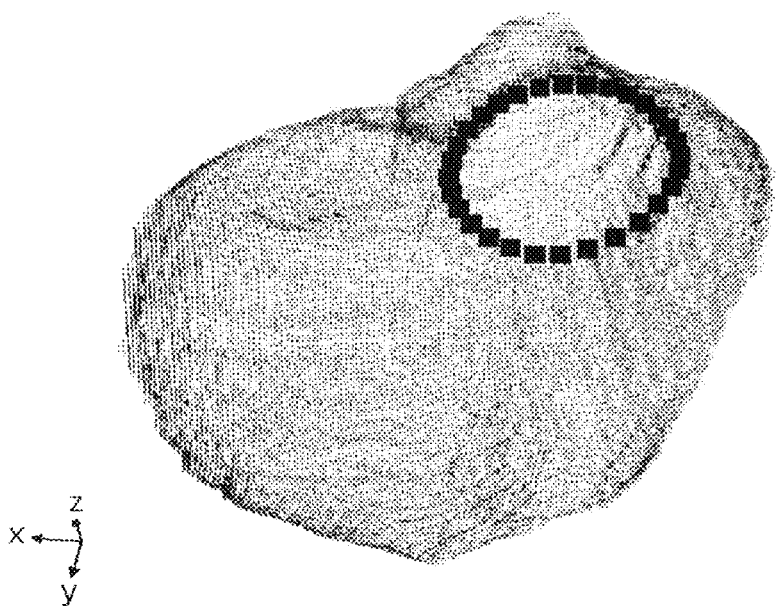
FIG. 30 is a diagram depicting a point set representing a boundary of a ventricle.

FIG. 30 illustrates an example of the point set generated in the step S71. In FIG. 30, the point set $p_{v,1}$, $p_{v,2}$, ..., $p_{v,j}$, ..., $p_{v,Mv}$ that represents the boundary of the ventricle is generated. Square diagrams represent the landmarks. Points included in the point set $p_{v,1}$, $p_{v,2}$, ..., $p_{v,j}$, ..., $p_{v,Mv}$ correspond to inner boundary points or outer boundary points.

The fourth calculator 123 removes, of the points included in the point set $p_{v,1}$, $p_{v,2}$, ..., $p_{v,j}$, ..., $p_{v,Mv}$ points that satisfy $h_1<0$, and generates a point set $p(bar)_{v,1}$, $p(bar)_{v,2}$, ..., $p(bar)_{v,j}$, ..., $p(bar)_{v,Mv(bar)}$ (step S73). The points that satisfy $h<0$ correspond to points that exist inside the 0 isosurface of the implicit function $h_1$. p(bar) represents a bar "-" is attached to p. Moreover, $_{v,Mv(bar)}$ represents a bar "-" is attached to a subscript M and v.

The fourth calculator 123 adds the landmarks $x_1$, $x_2$, ..., $x_i$, ..., $x_N$ to the generated point set $p(bar)_{v,1}$, $p(bar)_{v,2}$, ..., $p(bar)_{v,j}$, ..., $p(bar)_{v,Mv(bar)}$ (step S75).

In the third embodiment, $x_1 \pm \varepsilon_b n_1$, $x_2 \pm \varepsilon_b n_2$, ..., $x_i \pm \varepsilon_b n_i$, ..., $x_N \pm \varepsilon_b n_N$ are not added to the point set. This is because there are points in the vicinity of the landmarks.

The fourth calculator 123 sets a function value of the implicit function f (step S77). More specifically, the function value is set as follows:

$$f(\overline{p}_{v,j}) = \begin{cases} 1 & \text{when } \overline{p}_{v,j} \text{ is an outer boundary point} \\ -1 & \text{when } \overline{p}_{v,j} \text{ is an inner boundary point} \end{cases}$$

$$f(x_j) = 0$$

The fourth calculator 123 finds the implicit function f so that the function value becomes the value set in the step S77 (step S79), and stores data of the implicit function f in the fourth function storage unit 125. Then the processing returns to the calling-source processing.

In the step S79, as well as the first and second embodiments, the implicit function f is found by using TPS. When it takes time to find the implicit function f using TPS, the implicit function f may be found by a method, for example, described in the non-patent document 1. The disclosure of the non-patent document 1 is incorporated herein by reference.

Figure 31:
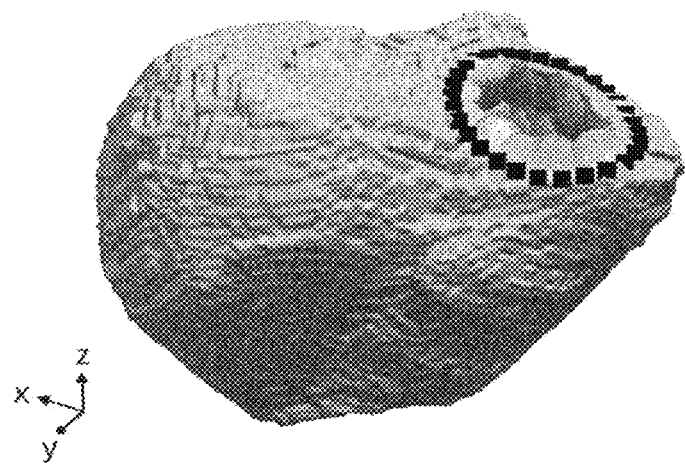
FIG. 31 is a diagram depicting a modified shape.

FIG. 31 illustrates a boundary formed by a point set that makes the value of the implicit function f equal to 0 (hereinafter, referred to as a 0 isosurface of the implicit function f). In FIG. 31, square diagrams represent the landmarks. Correction have been performed so that the boundary of the ventricle is located on the landmarks by the processing up to here, however, there are heart muscles also inside the landmarks (in other words, inside the valve annulus). Therefore, by the following processing, the heart muscles inside the valve annulus are removed.

Figure 32:
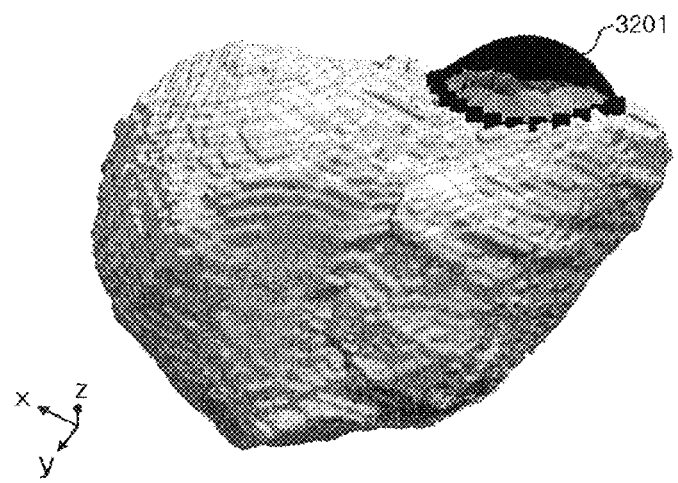
FIG. 32 is a diagram for explaining a closed surface generated by an implicit function $h_2$.

Returning to the explanation of FIG. 27, the third calculator 119 performs the closed surface generation processing (step S65). The closed surface generation processing is the same as the one explained in the second embodiment, and a detailed explanation is omitted. In the step S65, an implicit function $h_2$ for generating a closed surface is found assuming that $\varepsilon_b=1.0$ and D=0. FIG. 32 illustrates a surface formed by a point set that makes the value of the implicit function $h_2$ equal to 0 (hereinafter, referred to as a 0 isosurface of the implicit function $h_2$). In FIG. 32, square diagrams represent the landmarks, and the 0 isosurface of the implicit function $h_2$ 3201 corresponds to a closed surface with an ellipsoidal shape. The 0 isosurface of the implicit function $h_2$ 3201 passes through the landmark because D=0. Values of the implicit function $h_2$ are negative inside the closed surface, and values of the implicit function $h_2$ are positive outside the closed surface.

Then, the deletion unit 127 performs deletion processing based on data of the implicit function $h_2$ stored in the third function storage unit 121 and data of the implicit function f stored in the fourth function storage unit 125 (step S67), and stores volume data representing the shape after the deletion processing in the data storage unit 115.

The deletion processing is processing to remove, of the shape represented by the 0 isosurface of the implicit function f, a portion inside the 0 isosurface of the implicit function $h_2$. For example, a point set that satisfies the implicit function f=0 and the implicit function $h_2>0$ is found in the deletion processing, and volume data for the point set is stored in the data storage unit 115.

Figure 33:
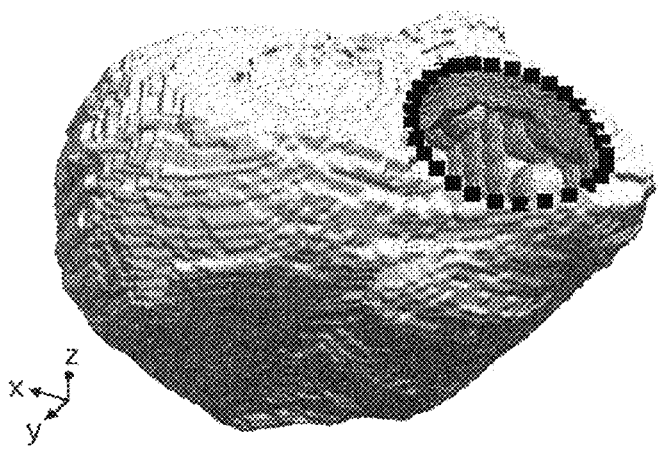
FIG. 33 is a diagram depicting a modified shape.

The output unit 117 outputs the volume data stored in the data storage unit 115 to the display device or the like (step S69). FIG. 33 illustrates an example of the volume data and the landmarks. As illustrated in FIG. 33, the heart muscles that were inside the valve annulus are removed, and the inside of the valve annulus is ventricular.

Although the embodiments of this invention were explained above, this invention is not limited to those. For example, the functional block configuration of the information processing apparatus 1 which is explained above, do not always correspond to actual program module configuration.

Moreover, the configurations of the respective data storages are mere example, and may be changed. Furthermore, as for the processing flow, as long as the processing results do not change, the turns of the steps may be exchanged or the steps may be executed in parallel.

For example, in the first embodiment, the turn of the division surface generation processing and the turn of the shape generation processing may be exchanged.

Even if landmarks are not deployed annularly, these embodiments may be applied if a division surface and a closed surface that pass through the landmarks can be generated.

Figure 34:
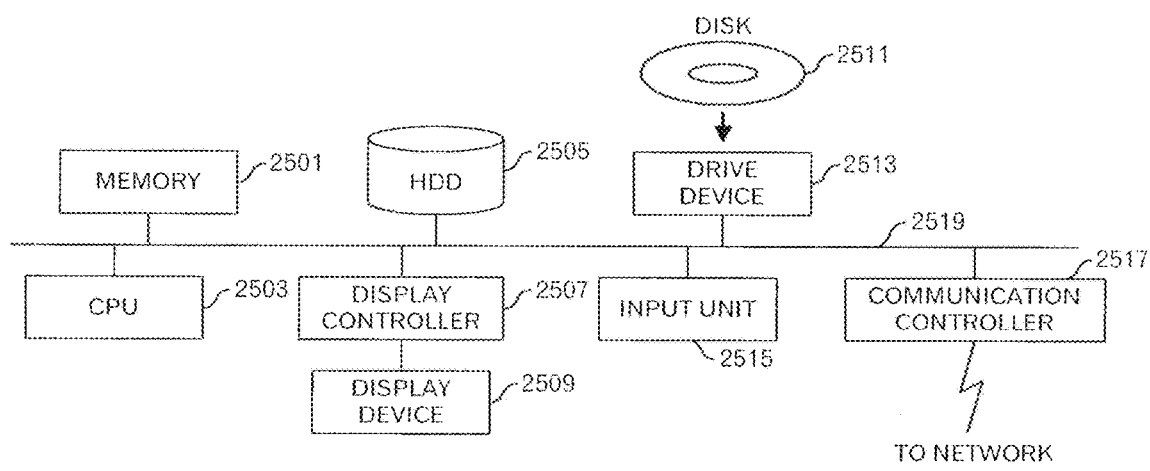
FIG. 34 is a functional block diagram of a computer.

In addition, the aforementioned the information processing apparatus 1 is computer device as shown in FIG. 34. That is, a memory 2501 (storage device), a CPU 2503 (processor), a hard disk drive (HDD) 2505, a display controller 2507 connected to a display device 2509, a drive device 2513 for a removable disk 2511, an input unit 2515, and a communication controller 2517 for connection with a network are connected through a bus 2519 as shown in FIG. 34. An operating system (OS) and an application program for carrying out the foregoing processing in the embodiments, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform necessary operations. Besides, intermediate processing data is stored in the memory 2501, and if necessary, it is stored in the HDD 2505. In these embodiments of this technique, the application program to realize the aforementioned processing is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the necessary application programs systematically cooperate with each other, so that various functions as described above in details are realized.

The aforementioned embodiments are summarized as follows:

A modelling apparatus relating to a first aspect of these embodiments includes: a memory; and a processor configured to use the memory and execute a process. And the process includes: (A) first calculating a first function for generating a closed surface that contains plural points that represent an annular structure in an object, based on positional information of the plural points; (B) generating a first point set that represents a boundary of the object, from plural tomographic images in each of which a first area occupied by the object is designated; (C) detecting points which are included in the first point set and located inside the closed surface by using the first function; (D) removing the detected points from the first point set to generate a second point set; and (E) second calculating a second function for generating a shape of the object using the second point set and the plural points.

By performing processing described above, it becomes possible to generate a high-accuracy object shape including an annular structure, because unwanted substances when generating the annular structure are removed.

Moreover, the aforementioned modelling apparatus may further include: (F) third calculating a third function for generating a surface that passes through the plural points; and (G) dividing the shape of the object, which is generated by using the second function, by the surface generated by using the third function. By performing the processing described above, it becomes possible to separate the object at a part that has an annular structure.

Moreover, the first calculating may include: (a1) first identifying, for each of the plural points, a third point set that includes a first point separated from the point in a positive direction of a normal for the point by a first distance, a second point separated from the point in the positive direction of the normal by a second distance, a third point separated from the point in the negative direction of the normal by the second distance, a fourth point separated from the point in a positive direction of a binormal for the point by a third distance, and a fifth point separated from the point in a negative direction of the binormal by the third distance; and (a2) first setting a function value for each point included in the identified third point set to calculate the first function based on the set function values. By performing the processing as described above, it becomes possible to properly remove unwanted substances when generating the annular structure, because an ellipsoidal closed surface is generated.

Moreover, the second calculating may include: (e1) second identifying, for each of the plural points, a fourth point set that includes a sixth point separated from the point in a positive direction of a normal for the point by a fourth distance, and a seventh point separated from the point in a negative direction of the normal by the fourth distance; and (e2) second setting a function value for each point included in the fourth point set, a function value for each of the plural points, and a function value for each point included in the second point set to calculate the second function based on the set function values. By performing the processing as described above, it becomes possible to properly generate a shape in the vicinity of the annular structure.

Moreover, the third calculating may include: (f1) third identifying, for each of the plural points, a fifth point set that includes an eighth point separated from the point in a positive direction of a binormal for the point by a fifth distance, and a ninth point separated from the point in a negative direction of the binormal by the fifth distance; and (f2) third setting a function value for each point included in the fifth point set and a function value for each of the plural points to calculate the third function based on the set function values. By performing the processing as described above, it becomes possible to suppress occurrence of concavity and convexity on the surface.

Moreover, the detecting comprises: (c1) detecting points which are included in the first point set and located inside the closed surface, based on whether or not values of the first function are greater than a predetermined value. By performing the processing as described above, it becomes possible to easily detect points located inside the closed surface.

Moreover, the first point set may include points which are included in the first area and adjacent to an area other than the first area, and points which are included in the area other than the first area and adjacent to the first area. By doing this, it becomes possible to generate the point set that represents the boundary of the object.

A modelling method relating to a second aspect of these embodiments includes: (H) first calculating a first function for generating a closed surface that contains plural points that represent an annular structure in an object, based on positional information of the plural points; (I) generating a first point set that represents a boundary of the object, from plural tomographic images in each of which a first area occupied by the object is designated; (J) detecting points which are included in the first point set and located inside the closed surface by using the first function; (K) removing the detected points from the first point set to generate a second point set; (L) and second calculating a second function for generating a shape of the object using the second point set and the plural points.

A modelling apparatus relating to a third aspect of these embodiments includes circuitry or a processor configured to: (M) calculate a first function for generating a closed surface that contains plural points that represent an annular structure in an object, based on positional information of the plural points; (N) generate a first point set that represents a boundary of the object, from plural tomographic images in each of which a first area occupied by the object is designated; (O) detect points which are included in the first point set and located inside the closed surface by using the first function; (P) remove the detected points from the first point set to generate a second point set; and (Q) calculate a second function for generating a shape of the object using the second point set and the plural points.

A modelling apparatus relating to a fourth aspect of these embodiments includes: (R) a first calculator that calculates a first function for generating a closed surface that contains plural points that represent an annular structure in an object, based on positional information of the plural points; (S) a generator that generates a first point set that represents a boundary of the object, from plural tomographic images in each of which a first area occupied by the object is designated; (T) a detector that detects points which are included in the first point set and located inside the closed surface by using the first function; (U) a removing unit that removes the detected points from the first point set to generate a second point set; and (V) a second calculator that calculates a second function for generating a shape of the object using the second point set and the plural points.

Incidentally, it is possible to create a program causing a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:
1. A modeling apparatus, comprising:
a memory configured to store positional information of a plurality of points that represent an annular structure in an object; and a processor coupled to the memory and configured to:
calculate a first function for generating data of a closed surface that contains the plurality of points, based on the positional information of the plurality of points;
generate data of first boundary points of the object, from data of a plurality of tomographic images in each of which a first area occupied by the object is designated, wherein the first boundary points correspond to the annular structure in the plurality of tomographic images, and the first boundary points include points which are included in the first area and are adjacent to a second area other than the first area, and points which are included in the second area and are adjacent to the first area;
detect, using the first function, second boundary points which are located inside the closed surface from among the first boundary points;
remove data of the detected second boundary points from the data of the first boundary points to generate data of third boundary points;
calculate a second function for generating data of a shape of the object, using the data of the third boundary points and the positional information of the plurality of points; and
store the data of the shape of the object, which is generated by using the second function, in the memory.

2. The modeling apparatus as recited in claim 1, wherein the processor is further configured to:
calculate a third function for generating data of a surface that passes through the plurality of points; and
divide the data of the shape of the object, which is stored in the memory, by the data of the surface generated by using the third function.

3. The modeling apparatus as recited in claim 1, wherein to calculate the first function, the processor is configured to:
identify, for each of the plurality of points, data of a first point set that includes a first point separated from the point in a positive direction of a normal for the point by a first distance, a second point separated from the point in the positive direction of the normal by a second distance, a third point separated from the point in a negative direction of the normal by the second distance, a fourth point separated from the point in a positive direction of a binormal for the point by a third distance, and a fifth point separated from the point in a negative direction of the binormal by the third distance; and
set a function value for each point included in the first point set to calculate the first function based on the set function values.

4. The modeling apparatus as recited in claim 1, wherein to calculate the second function, the processor is configured to:
identify, for each of the plurality of points, data of a second point set that includes a sixth point separated from the point in a positive direction of a normal for the point by a fourth distance, and a seventh point separated from the point in a negative direction of the normal by the fourth distance; and
set a function value for each point included in the second point set, a function value for each of the plurality of points, and a function value for each of the third boundary points to calculate the second function based on the set function values.

5. The modeling apparatus as recited in claim 2, wherein to calculate the third function, the processor is configured to:
identify, for each of the plurality of points, data of a third point set that includes an eighth point separated from the point in a positive direction of a binormal for the point by a fifth distance, and a ninth point separated from the point in a negative direction of the binormal by the fifth distance; and
set a function value for each point included in the third point set and a function value for each of the plurality of points to calculate the third function based on the set function values.

6. The modeling apparatus as recited in claim 1, wherein the processor detects the second boundary points based on whether or not values of the first function are greater than a predetermined value.

7. A modeling method using a computer including a memory configured to store positional information of a plurality of points and a processor coupled to the memory, the modeling method comprising:
calculating, by the processor, a first function for generating data of a closed surface that contains the plurality of points that represent an annular structure in an object, based on the positional information of the plurality of points;
generating, by the processor, data of first boundary points of the object, from data of a plurality of tomographic images in each of which a first area occupied by the object is designated, wherein the first boundary points correspond to the annular structure in the plurality of tomographic images, and the first boundary points include points which are included in the first area and are adjacent to a second area other than the first area, and points which are included in the second area and are adjacent to the first area;
detecting, by the processor using the first function, second boundary points which are located inside the closed surface from among the first boundary points;
removing, by the processor, data of the detected second boundary points from the data of the first boundary points to generate data of third boundary points;
calculating, by the processor, a second function for generating data of a shape of the object, using the data of the third boundary points and the position information of the plurality of points; and
storing in the memory, by the processor, the data of the shape of the object, which is generated using the second function.

8. A non-transitory computer-readable storage medium storing a program that causes a computer including a memory configured to store positional information of a plurality of points and a processor coupled to the memory to execute a modeling process, the modeling process comprising:
calculating, by the processor, a first function for generating data of a closed surface that contains the plurality of points that represent an annular structure in an object, based on the positional information of the plurality of points;
generating, by the processor, data of first boundary points of the object, from data of a plurality of tomographic images in each of which a first area occupied by the object is designated, wherein the first boundary points correspond to the annular structure in the plurality of tomographic images, and the first boundary points include points which are included in the first area and are adjacent to a second area other than the first area, and points which are included in the second area and are adjacent to the first area;

detecting, by the processor using the first function, second boundary points which are located inside the closed surface from among the first boundary points;

removing, by the processor, data of the detected second boundary points from the data of the first boundary points to generate data of third boundary points;

calculating, by the processor, a second function for generating data of a shape of the object, using the data of the third boundary points and the position information of the plurality of points; and storing in the memory, by the processor, the data of the shape of the object, which is generated using the second function.

* * * * *